United States Patent
Ball

[19]

[11] Patent Number: 5,987,970
[45] Date of Patent: Nov. 23, 1999

[54] ROTATIONAL VISCOSITY MEASUREMENT APPARATUS

[75] Inventor: Dean M. Ball, Gainesville, Ga.

[73] Assignee: Cannon Instrument Company, State College, Pa.

[21] Appl. No.: 09/131,947

[22] Filed: Aug. 10, 1998

[51] Int. Cl.⁶ .......................... G01N 11/14; G01N 33/48; H01J 5/16
[52] U.S. Cl. ......................... 73/54.28; 73/54.34
[58] Field of Search ............... 73/54.28, 54.33, 73/54.34, 54.38

[56] References Cited

U.S. PATENT DOCUMENTS

| | | | |
|---|---|---|---|
| 1,192,861 | 8/1916 | Carmichael et al. | 73/59 |
| 1,236,706 | 8/1917 | Grosvenor | 73/59 |
| 1,281,042 | 10/1918 | MacMichael | 73/59 |
| 1,334,856 | 3/1920 | Hayes et al. | 73/59 |
| 1,817,739 | 8/1931 | Dintilhac | 73/59 |
| 1,930,629 | 10/1933 | Stephens | 265/11 |
| 2,239,726 | 4/1941 | Martin | 265/11 |
| 2,354,299 | 7/1944 | Bays | 265/11 |
| 2,382,979 | 8/1945 | Demb | 73/59 |
| 2,638,779 | 5/1953 | Wilson | 73/57 |
| 2,657,572 | 11/1953 | Fann | 73/59 |
| 2,713,790 | 7/1955 | Barber et al. | 73/60 |
| 2,977,790 | 4/1961 | Dubský et al. | 73/60 |
| 3,126,735 | 3/1964 | Vogtle et al. | 73/59 |
| 3,162,038 | 12/1964 | Roberson et al. | 73/59 |
| 3,212,319 | 10/1965 | Levy et al. | 73/15.4 |
| 3,465,575 | 9/1969 | Kepes | 73/60 |
| 3,545,257 | 12/1970 | Zemp et al. | 73/59 |
| 3,667,286 | 6/1972 | Kaufman et al. | 73/59 |
| 3,722,262 | 3/1973 | Gilinson, Jr. et al. | 73/59 |
| 3,803,903 | 4/1974 | Lin | 73/59 |
| 3,875,791 | 4/1975 | Fitzgerald et al. | 73/59 |
| 3,935,726 | 2/1976 | Heinz | 73/60 |
| 3,935,729 | 2/1976 | McCarthy | 73/60 |
| 3,939,690 | 2/1976 | Kuss et al. | 73/9 |
| 4,045,999 | 9/1977 | Palmer | 73/59 |
| 4,077,252 | 3/1978 | Stutz et al. | 73/59 |

(List continued on next page.)

FOREIGN PATENT DOCUMENTS

| | | |
|---|---|---|
| 711446 | 10/1941 | Germany . |
| 404054435 | 2/1992 | Japan . |
| 433381 | 6/1974 | Russian Federation . |
| 0851190 | 7/1981 | Russian Federation . |
| 1224674 | 4/1986 | Russian Federation . |
| 1627919 | 2/1991 | Russian Federation . |
| 684935 | 12/1952 | United Kingdom . |

*Primary Examiner*—Hezron Williams
*Assistant Examiner*—J. David Wiggins
*Attorney, Agent, or Firm*—Seidel, Gonda, Lavorgna & Monaco, PC

[57] ABSTRACT

A rotational viscometer is disclosed for measuring the viscosity of a rotating fluid. The viscometer includes a measurement disk that is positioned within the rotating fluid and is interconnected via a shaft with a measurement arm mounted within a housing. A light source is mounted within the housing and emits a beam of light onto one or more light receivers. The light receivers provide an output signal that is a function of the amount of light received. An end of the measurement arm is movably disposed between the light source and the light receivers. Pivoting of the measurement arm controls the amount of light received by the light receivers. A signal processor receives the output signals from the light receivers and determines a restorative signal therefrom. The restorative signal is provided to a balance coil which is located adjacent a permanent magnet. The balance coil generates an electromagnetic field as a, function of the restorative signal. An adjustment shaft has one end engaged with the balance coil and the other end attached to the measurement arm. The generation of an electromagnetic field in the balance coil causes the adjustment shaft to translate resulting in pivoting of the measurement arm about its center of rotation in an opposite direction from its initial displacement. An output device receives the restorative signal and determines the viscosity of the fluid therefrom.

19 Claims, 4 Drawing Sheets

U.S. PATENT DOCUMENTS

| | | | |
|---|---|---|---|
| 4,175,425 | 11/1979 | Brookfield | 73/59 |
| 4,181,023 | 1/1980 | Clamroth et al. | 73/432 R |
| 4,352,287 | 10/1982 | Orth et al. | 73/60 |
| 4,488,427 | 12/1984 | Matusik et al. | 73/59 |
| 4,566,181 | 1/1986 | Matusik et al. | 29/602 R |
| 4,726,220 | 2/1988 | Feier et al. | 73/59 |
| 5,120,951 | 6/1992 | Small | 250/227.21 |
| 5,167,143 | 12/1992 | Brookfield | 73/54.23 |
| 5,187,975 | 2/1993 | Chiba et al. | 73/54.01 |
| 5,269,174 | 12/1993 | Chiba et al. | 73/54.01 |
| 5,365,777 | 11/1994 | Layton | 73/54.28 |
| 5,483,840 | 1/1996 | Chang et al. | 73/861.71 |
| 5,503,003 | 4/1996 | Brookfield | 73/54.32 |
| 5,513,517 | 5/1996 | Van Meter et al. | 73/54.28 |
| 5,531,102 | 7/1996 | Brookfield et al. | 73/54.32 |
| 5,535,619 | 7/1996 | Brookfield | 73/54.33 |
| 5,763,766 | 6/1998 | Robinson | 73/54.33 |
| B1 4,448,061 | 11/1995 | Brookfield | 73/54.33 |

ROTATIONAL VISCOSITY MEASUREMENT APPARATUS

FIELD OF THE INVENTION

The present invention relates to a device for measuring the rheological properties of a fluid and, more particularly, to a rotational viscometer for measuring a fluid's viscosity.

BACKGROUND OF THE INVENTION

Many commercial and industrial processes require precise knowledge of the physical properties of substances being used in those processes in order to operate efficiently. For example, it is important to accurately determine the rheological properties, such as viscosity, of a liquid in food, cosmetics, paint, ink and lubricant industries. For example, controlling the viscosity of inks is very important for the proper performance of high speed printers. Also, the performance of paint sprayers and similar high speed paint application equipment requires that the paint viscosity be accurately controlled. In general, as industrial processes become more accurate and made to operate at higher speed, an accurate assessment of the viscosity of liquids used in the process is more and more important.

The viscosity of a fluid is a measure of the fluid's resistance to flow. Several commercially available conventional devices (viscometers) measure the viscosity of a fluid sample by rotating the sample within a container. A disk is suspended within the fluid sample and connected to a measurement apparatus. The viscosity of the fluid causes the suspended disk to rotate. The device calculates the viscosity of the fluid by measuring the amount that the suspended disk rotates, since the rotational force imposed on the disk by the rotating fluid is proportional to the fluid's viscosity.

In order to measure the rotation of the suspended disk, conventional viscometers incorporate mechanical components, such as a coiled spring, to determine the angular displacement of the disk. Measurements made with these types of systems, however, are subject to errors. For example, errors can result from the nonlinear characteristics of the spring caused by manufacturing imperfections, and from variations in spring tension due to temperature changes. It is common for the accuracy of these mechanical viscometers to be about one part in 100 or about 1%.

Additionally, the limited dynamic range of the spring requires that the viscometer be calibrated using a calibration standard that has a viscosity closely approximately the viscosity of the sample being measured. As is readily apparent, since the sample's viscosity is not known, the selection of the calibration standard is subject to error.

Another problem with mechanical spring-type designs is that the springs are typically designed to measure small forces. As such, these devices can be easily damaged if an excessive force is applied.

Other types of viscometers currently available operate by rotating a disk within a fluid sample in a stationary container. The drag imposed on the disk by the fluid sample is proportional to the viscosity of the fluid sample. These types of viscometers suffer similar deficiencies as with the viscometers which rotate the fluid sample.

A need, therefore, exists for an improved rotational viscometer which provides accurate viscosity measurements for a fluid sample and is easy to calibrate.

SUMMARY OF THE INVENTION

The present invention relates to a rotational viscometer for measuring the viscosity of a fluid. The fluid is contained within a container that is rotated by a motor. A measurement disk is positioned within the rotating fluid. A shaft extends upward from the measurement disk and attaches to a support block. The support block and the measurement disk have coincident centers of rotation.

Two displacement shafts extend upward from the support disk and attach to a measurement arm which is rotatably mounted within a housing. The displacement shafts attach to the measurement arm on opposite sides of the measurement arm's center of rotation.

A light source is mounted within the housing and emits a beam of light onto one or more light receivers. The light receivers provide an output signal which is a function of the amount of light received. One end of the measurement arm is movably disposed between the light source and the light receivers, preventing at least a portion of the emitted light from being received by the light receivers.

A signal processor receives the output signals from the light receivers and calculates a restorative signal as a function of the output signals. The restorative signal is then sent to a balance coil which is located adjacent a permanent magnet. The balance coil generates an electromagnetic field when the displacement signal's value is non-zero. The electromagnetic field causes an adjustment shaft to translate. One end of the adjustment shaft is attached to the measurement arm. Hence, translation of the attachment shaft causes the measurement arm to rotate about its center of rotation in a direction opposite from its initial displacement.

The restorative signal is also transmitted to an output device, such as a digital computer or a display. The viscosity of the fluid is determined from the restorative signal and stored on the computer and/or displayed.

The foregoing and other features and advantages of the present invention will become more apparent in light of the following detailed description of the preferred embodiments thereof, as illustrated in the accompanying figures.

BRIEF DESCRIPTION OF THE DRAWINGS

For the purpose of illustrating the invention, the drawings show a form of the invention which is presently preferred. However, it should be understood that this invention is not limited to the precise arrangements and instrumentalities shown in the drawings.

DESCRIPTION OF THE INVENTION

Figure 1:
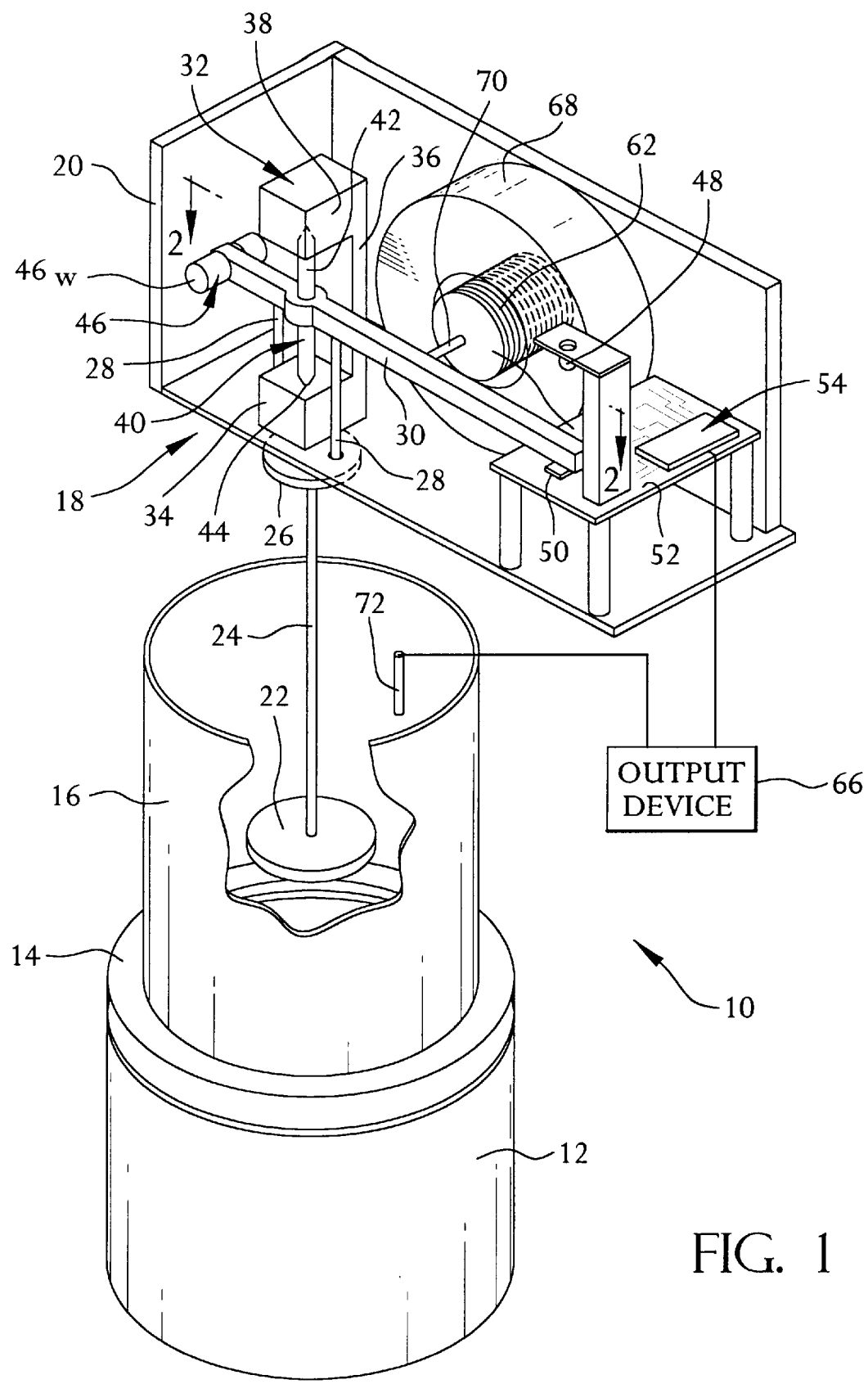
FIG. 1 is an isometric view of a rotational viscometer according to the present invention.

Referring now to the drawings, wherein like reference numerals illustrate corresponding or similar elements throughout the several views, FIG. 1 is an isometric view of a rotational viscometer 10 according to the present invention. The viscometer 10 includes a motor 12 operably connected to a turntable 14 to rotate the turntable 14 at a precise rate of speed. A preferred motor is a stepper motor having a speed range of from 0 to about 200 revolutions per minute. One suitable stepper motor is model RAS-3229-002 manufactured by Hurst Manufacturing Division, Emerson Electric Co., Princeton, Ind. A container 16 is removably positioned on the center of the turntable 14, and contains the sample of fluid to be tested by the viscometer 10.

The container 16, turntable 14, and motor 12 are all preferably located beneath or proximate to a measurement device 18. The measurement device 18 includes a housing 20 which surrounds and supports several of the components that perform the viscosity measurement and excludes ambient light from interfering with the light receiver 50. The details of the housing 20 are not important to the overall invention except as noted herein.

The measurement device 18 also includes a measurement disk 22 located outside the housing 20 and within the container 16. The measurement disk 22 is adapted to be immersed within the fluid sample being tested. The measurement disk preferably has a diameter ranging from about 10 mm to about 50 mm, a thickness of about 1 mm, is made from an inert metal, such as 316 stainless steel, and has a surface finish of 4 microinches or better. The measurement disk 22 is attached to an end of a shaft 24 which extends upward and out of the container 16. The attachment of the measurement disk 22 to the shaft 24 can be through any conventional means known to those skilled in the art. The shaft is preferably made from hardened steel.

A support block 26 is connected to a top end of the shaft 24 by any conventional means. The support block 26 is illustrated in FIG. 1 as being located outside the housing 20. However, it is also contemplated that the support block 26 can be located within the housing 20 if desired. The connections between the measurement disk 22, shaft 24 and support block 26 are substantially rigid, so that rotation of the measurement disk 22 produces concomitant rotation of the support block 26. As illustrated, the support block 26 is preferably in the shape of a disk with its center mounted coincident with the center of rotation of the shaft 24 and measurement disk 22. The support block 26 is preferably made from aluminum or steel material. It should be understood that the support block 26 can be eliminated in the invention so long as the torque generated by the measurement disk 22 is accurately transmitted to the measurement device 18.

Two displacement shafts 28 extend from the top of the support block 26. The displacement shafts 28 preferably are mounted on diametrically opposite sides of the support block 26 at locations equidistant from the center of rotation of the support block 26. The displacement shafts 28 are preferably made from stainless steel material and have a diameter of about 2 mm. The displacement shafts 28 extend upward from the support block 26 and into the housing 20 through holes (not shown) formed in the housing 20. The holes are sized to permit a small amount of lateral motion of the displacement shafts 28. As will be discussed in more detail below, when the support block 26 rotates, the displacement shafts 28 move between approximately two and approximately five degrees along arc sectors around a common axis. The holes formed in the housing are over-sized or slotted to accommodate this motion. However, the holes should not be too large since the holes also serve to limit the motion of the displacement shafts 28 to prevent damage to the measurement device 18. The displacement shafts 28 attach to a measurement arm 30 located within the housing 20. The measurement arm 30 will be discussed in more detail below. The support block 26 and displacement shafts 28 are used in the present invention to transfer torque to the measurement arm 30.

A bearing block 32 is mounted to the housing adjacent the two displacement shafts 28. The bearing block 32 preferably includes a lower portion 34, a vertical portion 36, and an upper portion 38 configured to form a C-shaped structure. A vertical pivot shaft 40 is rotatably mounted to the bearing block 32. The vertical pivot shaft 40 is preferably made from hardened steel and includes a center shank portion 42 and two polished conical ends 44. One of the conical ends 44 engages with a jeweled bearing (not shown) mounted in the upper portion 38 of the bearing block 32. The other conical end 44 engages with a jeweled bearing (not shown) mounted in the lower portion 34 of the bearing block 32. The pivot shaft and jeweled bearings are commercially available from Sman Parts Inc., Miami Lakes Fla. Preferred models include the Vee Jewel Assembly, E-VIA-7 and the Vee Jewel Pivot Shaft, E-VJPX-7D. The vertical pivot shaft 40 is designed to pivot or rotate about a vertical axis of rotation between the jeweled bearings of the bearing block 32. The vertical axis of rotation is preferably coincident with the axis of rotation of the measurement disk 22 and support block 26. The jeweled bearings and conical surfaces 44 provide very low rotational friction, thus allowing the vertical pivot shaft 40 to rotate freely. Alternately, the jeweled bearings could be attached to a portion of the housing, eliminating the need for the bearing block 32.

The measurement arm 30 is fixedly mounted to the center shank portion 42 of the vertical pivot shaft 40, thereby permitting the measurement arm 30 to pivot with respect to the bearing block 32. The measurement arm 30 extends laterally from the sides of the vertical pivot shaft 40. The displacement shafts 28 are attached to the measurement arm 30 on either side of the vertical pivot shaft 40. As such, rotation of the support block 26 causes the displacement shafts 28 to pivot the measurement arm 30 about its pivot axis which is coincident with the center of rotation of the vertical pivot shaft 40 and, in the embodiment illustrated, the measurement disk 22. The measurement arm 30 is preferably made from aluminum, and is about 90 mm long, about 4 mm wide and about 5 mm thick.

A counterbalance 46 is mounted on a first end of the measurement arm 30. The counterbalance 46 includes one or more removable weights 46$_W$ attached to the measurement arm 30. The counterbalance 46 permits the measurement arm 30 to be precisely balanced about its center of rotation. Precise balancing of the measurement arm 30 permits that measurement device 18 to be essentially immune to most vibrations and allows for more accurate measurements.

A light source 48, such as a light emitting diode (LED), is mounted approximately 2 cm to 3 cm above a second end of the measurement arm 30. The light source 48 is configured to emit light downward toward the measurement arm 30. Two light receivers 50, such as silicon photodiodes, are located below the second end of the measurement arm 30 and the light source 48. (Only one light receiver is shown in FIG. 1. The second light receiver lies adjacent to the first.) The light receivers 50 are located so as to receive light from the light source 48. When the measurement shaft 30 is in a rest position (i.e., not pivoted about its pivot axis), the measurement arm 30 preferably prevents light from the light source 48 from completely illuminating the light receivers 50. (See FIG. 2A.) That is, the measurement arm 30 partially obscures the light receivers 50. In this state, the light receivers 50 each receive an equal amount of light from the light source 48. When the measurement arm 30 is pivoted (i.e., in a non-zero state), one light receiver will receive more light than the other. (See, FIGS. 2B and 2C.) Each light receiver 50 outputs a current whose amplitude is representative of the amount of light received. A preferred diode is a model VTD34 made by EG&G Optoelectronics, Vactec Division, and available from Newark Electronics Part Number 52F8764.

Figure 3:
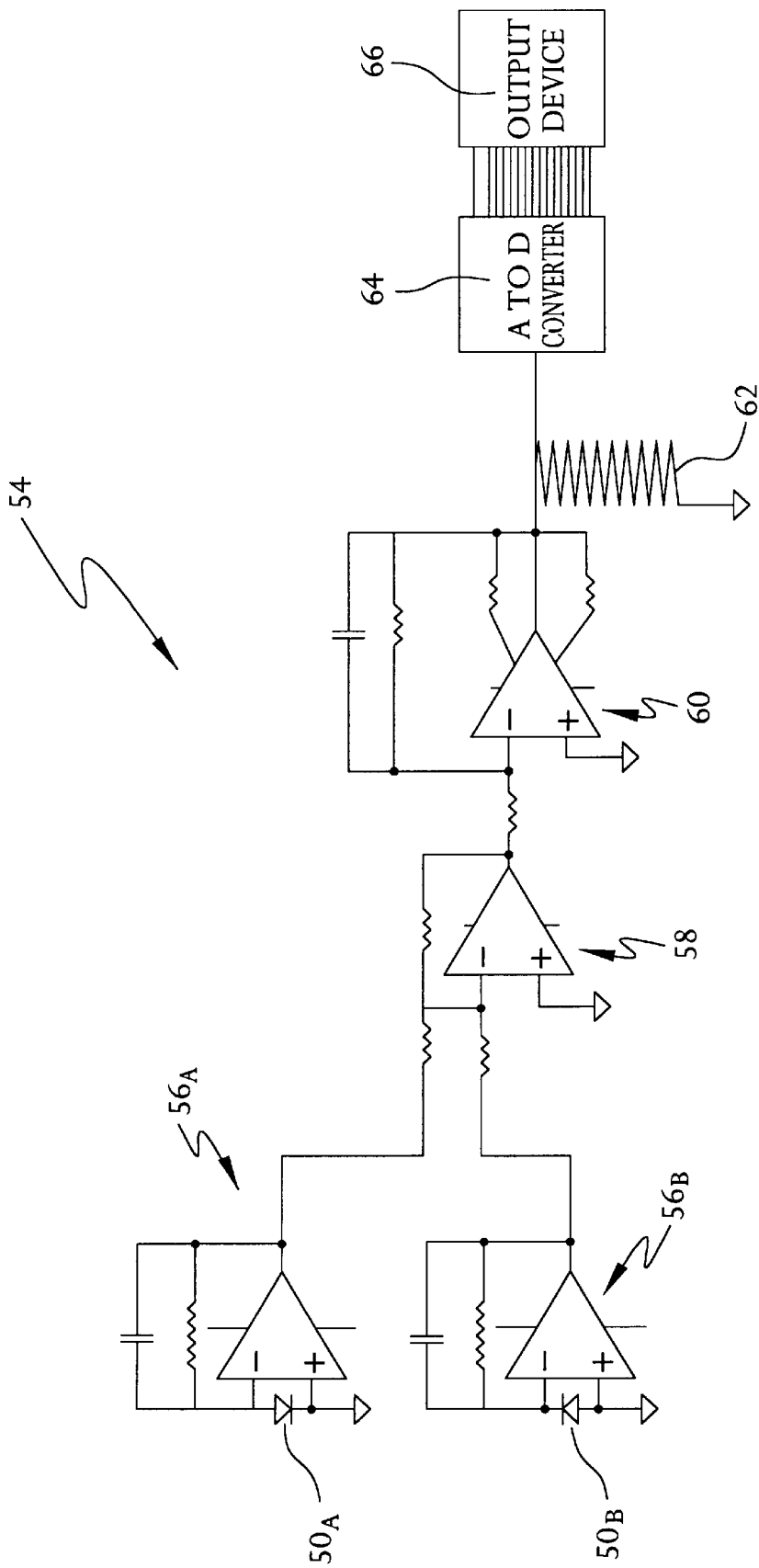
FIG. 3 is a schematic of a preferred measurement circuitry for use in the present invention.

The light receivers 50 are preferably mounted to a printed circuit board 52 and electrically connected in opposite polarity to measurement circuitry 54 (e.g., a signal processor) which is mounted on the printed circuit board 52. The measurement circuitry 54 is illustrated only generally in FIG. 1. A schematic representation of one preferred embodiment of the measurement circuitry 54 is shown in FIG. 3. As shown in the schematic, each light receiver (identified by the numerals $50_A$ and $50_B$) is electrically connected to a current-to voltage converter $56_A$, $56_B$. The current-to-voltage converters $56_A$, $56_B$ transform the current received from the light receivers $50_A$ and $50_B$ into a voltage. However, since the light receivers $50_A$ and $50_B$ are connected in opposite polarity, one converter $56_A$ will output a positive voltage and the other converter $56_B$ will output a negative voltage.

The voltage outputs from the converters $56_A$, $56_B$ are applied to a summing amplifier 58 which adds the voltages. The output from the summing amplifier 58 is then fed into a power amplifier 60 which amplifies the summed voltage. A restorative signal is output from the power amplifier 60 and sent to a balance coil 62 and to an analog-to-digital converter 64. The analog-to-digital converter 64 transforms the voltage into a digital signal which is transmitted to an output device, such as a digital computer or display (generally identified by the number 66). The digital computer or display 66 determines or provides a read-out of the viscosity of the sample which is a function of the digitized voltage value.

There are a variety of methods known to those skilled in the art for converting a voltage to a viscosity. For example, conventional instruments calibrate the measurement devices by using a liquid having a known viscosity which is run as a standard or reference. The present invention can also use this conventional method for calibrating the measurement device. However, the present invention can be calibrated by an alternate method. Since the measurement disk 22 does not rotate (i.e., is not driven), it is possible to rotate the entire measurement device 18 by 90 degrees so that the measurement disk 22 and support block 26 are facing the operator. In this position, the measurement arm 30 is horizontal and, assuming the measurement arm is balanced with respect to its axis of rotation, the device can be calibrated by hanging a small weight at a fixed distance from the center of rotation, similar to calibrating an analytical balance. For example, a 1.000 gram weight could be hung from the support block at a location 10.000 mm from its center. This would provide a torque of 1.000 grams-centimeters which could then be used to calibrate the electronics. This method of calibration eliminates the need to have a liquid sample available, and also permits testing of the linearity of the instrument by hanging various known weights on the support block.

Referring back to FIG. 1, the balance coil 62 is located within an air gap of a permanent magnet 68. A suitable balance coil 62 and magnet is available from Quam Chicago, Ill., model 8C10Z45B. In one embodiment, the preferred magnet is a ceramic magnet, and the coil is a one inch diameter voice coil with an impedance of 40 ohms. Voice coil assemblies and their operation are well known in the art and include a coil movably located within an air gap in a magnet. When a voltage is supplied to the coil, a magnetic field is created that causes the coil and anything attached to it to move relative to the magnet. An adjustment shaft 70 engaged with within the balance coil 62. One end of the adjustment arm is mounted to the measurement arm 30. The balance coil 62 is energized by a restorative signal of a non-zero voltage from the power amplifier 60. Energizing the balance coil 62 creates an electromagnetic field that causes the adjustment shaft 70 to translate laterally. The direction and amount of lateral movement of the adjustment shaft 70 is proportional to the polarity and amplitude of the voltage transmitted to the balance coil 62. In the embodiment illustrated, the balance coil 62 is configured to translate the adjustment shaft 70 in an opposite direction from the direction of rotation of the measurement arm 30. As such, since the adjustment shaft 70 is attached to the measurement arm 30, the movement of the adjustment shaft 70 forces the measurement arm 30 to move back toward its non-rotated or zero state. The amount of the counter-rotating (restoring) force produced by the adjustment shaft 70 is proportional to the amount that the measurement arm 30 pivots which, in turn, is a function of the viscosity of the liquid being measured.

The details of the present invention will become more apparent after the following discussion of the operation of an exemplary embodiment of the rotational viscometer 10 according to the present invention.

A fluid sample whose viscosity is to be measured is placed within the container 16 which is then placed on the turntable 14. The measurement disk 22 and shaft 24 are lowered into the fluid sample. The motor 12 is started causing the container 16 and liquid to rotate at a precise rate of speed. The viscosity of the liquid urges the measurement disk 22 to rotate in the same direction as the liquid. The rotation of the measurement disk 22 causes concomitant rotation of the shaft 24 and support block 26. The displacement shafts 28, which are mounted to the support block 26, move with the support block 26 about its axis of rotation. The displacement shafts 28, in turn, pivot the measurement arm 30 and vertical pivot shaft 40 about their center of rotation.

Figure 2C:
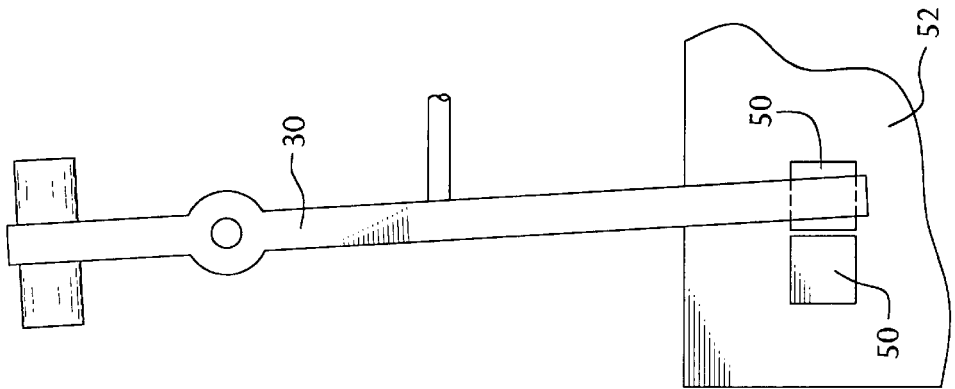
FIG. 2C is a partial view of the measurement arm in a second deflected state.
Figure 2B:
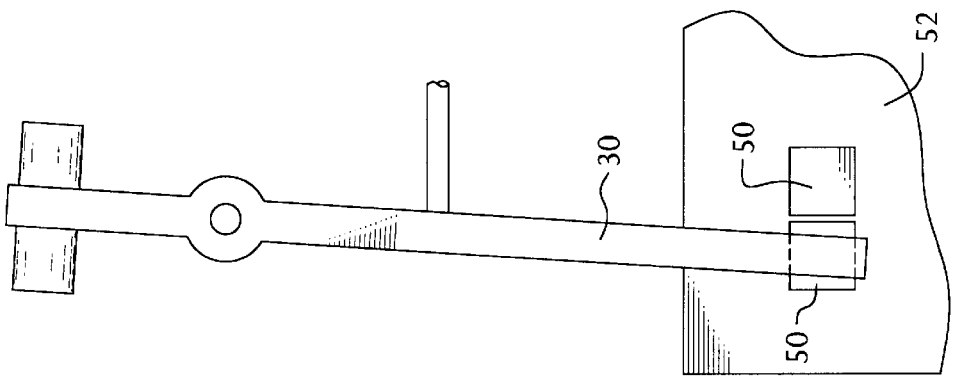
FIG. 2B is a partial view of the measurement arm in a first deflected state.
Figure 2A:
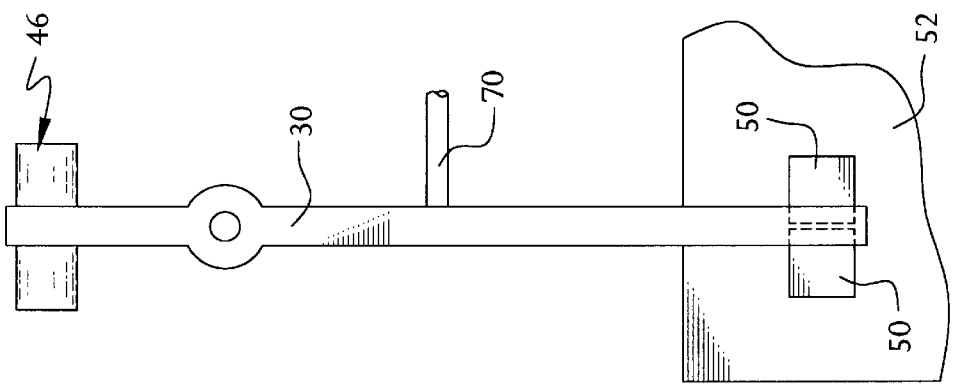
FIG. 2A is a partial view of a measurement arm according to the present invention in a non-deflected or zero state.

Referring to FIG. 2A, before the fluid sample is rotated, the second end of the measurement arm is in its rest position which prevents the light emitted from the light source 48 from completely illuminating the light receivers 50. In this state, the light receivers 50 each receive the same amount of light. The measurement circuitry 54 receives signals from the light receivers ($50_A$, $50_B$ in FIG. 3) representing the amount of current received. Since the light receivers $50_A$, $50_B$ receive the same amount of light, the currents generated by the light receivers $50_A$, $50_B$ are equal, although opposite in polarity. The currents are converted to voltages and summed by the summing amplifier 58, resulting in an output of zero volts. Since the output of the summing amplifier 58 is zero, there is no signal to provide to the balance coil 62 and the output device 66 (e.g., digital computer or the display). (In actuality, the circuitry provides a restorative signal with zero voltage to the balance coil 62 and output device 66.) As a result, no electromagnetic field is generated around the adjustment shaft 70.

Referring now to FIG. 2B, when the container 16 containing the fluid sample is rotated, the displacement shafts 28 pivot the measurement arm 30 about its axis of rotation causing the second end of the measurement arm 30 to overlie one light receiver 50 more than the other. As a result, the light receivers $50_A$, $50_B$ do not receive the same amount of light and, therefore, provide different currents to the measurement circuitry 54. More specifically, the current received from light receivers $50_A$ differs in both amplitude and polarity from the current received from light receiver $50_B$. The currents are converted to a voltage by the current-to-voltage converters $56_A$, $56_B$. The voltages are summed by the summing amplifier 58 and output as a non-zero voltage. The voltage output of the summing amplifier 58 is then amplified by the power amplifier 60 and provided as a restorative signal to the balance coil 62. The balance coil 62 generates an electromagnetic field that is a function of the voltage. The electromagnetic field forces the adjustment shaft 70 to translate, urging the measurement arm 30 to counter-pivot back toward its rest position. The amount that the adjustment shaft 70 translates is a function of the amplitude of the displacement signal. The polarity of the restorative signal determines the direction that the adjustment shaft 70 translates.

If the measurement arm 30 overshoots its rest position, the second end of the measurement arm 30 would then alter the amount of light being received by the photodiode as shown in FIG. 2C. The measurement circuitry 54 outputs a displacement signal based on the new currents received from the light receivers 50 calculated to drive the measurement arm 30 back to its rest position. The measurement arm 30 is part of a negative feedback loop that includes the photodiodes 50, the amplifiers 58, 60, and magnet and coil assembly. The gain of this loop is adjusted so that the loop is critically damped. That is, the gain can be increased or decreased so that the when the measurement arm 30 is disturbed, it will be restored to its original position (zero state) preferably within one or two oscillations. When the loop is adjusted properly, a stable value for the viscosity of the liquid can be read from the electronics. If the gain is too high, the measurement arm will oscillate continually. If the gain is too low, the sensitivity of the instrument will be compromised.

The measurement circuitry 54 also converts the non-zero restorative signal output from the power amplifier 60 to a digital signal which is transmitted to the output device 66. Since the digital signal is representative of the viscosity of the fluid sample, the signal can then be converted to an accurate viscosity value for storage and/or display.

In order to yield extremely accurate measurements, the temperature of the fluid sample must be held constant to a very precise level, for example, within at least 0.01 degrees Celsius. This can be achieved through any conventional means, such as environmental control (e.g., temperature bath). Those skilled in the art will be well aware of the various temperature control and monitoring devices that can be incorporated into the present invention.

Alternatively, it may be desirable to measure the temperature of the sample and, by comparison with known temperature/viscosity relationships stored in a computer program, accurately calculate the viscosity. In this embodiment, the class of the fluid sample would have to be known and the computer program would have to apply appropriate corrections. For example, hydrocarbon oils, silicon oils and polymer solutions each have a fairly well known and/or predictable viscosity/temperature relationship. The viscosity/temperature relationships would be stored on a computer and activated by the operator for the fluid sample being tested.

Referring back to FIG. 1, in order to measure the temperature of the sample accurately, a temperature probe 72 is provided and immersed in the fluid sample. The temperature probe 72 generates a signal which is sent to the measurement circuitry 54 and/or the digital computer.

While the invention has been described with the light source 48 and light receivers 50 located adjacent to the second end of the measurement arm 30, the light source 48 and light receivers 50 may be placed at any alternate position along the measurement arm 30. The measurement arm 30 need not be formed as an elongated rod as depicted in the preferred embodiment, but may take on any suitable shape which permits rotation of the measurement arm 30 to vary the amount of light that is received by the light receivers 50.

Also, while the above discussion has described the invention as being useful for testing fluid samples, it should be recognized that the invention can be used directly on production fluids to provide a periodic or constant viscosity reading.

It is also contemplated that the measurement arm 30 can be configured to completely prevent illumination of the light receivers 50 when in its rest position. In this embodiment, no current would be sent to the measurement circuitry 54 when the sample is not being rotated. Upon rotation, one of the light receivers 50 would receive more light than the other as described above.

In order to provide the viscometer 10 with the maximum amount of sensitivity and the largest dynamic range, it is important that the balance coil 62 and the measurement arm 30 are properly adjusted so as to locate the measurement arm 30 directly over the two photodiodes 50 when there is little or no force on the coil.

As discussed above, any attempt to move the measurement arm 30, such as when a liquid is rotating around the measurement disk, will cause the measurement arm 30 to move slightly. The measurement circuitry immediately attempts to restore the measurement arm 30 to its non-deflected position. The amount of restoring force is proportional to the voltage applied to the coil 62 and the viscosity of the liquid. In a properly operating system, the movement of the balance coil, measurement arm and measurement disk will be so small as to not be apparent to the casual observer. While one embodiment of the present invention has been disclosed with two photodiodes, it is also contemplated that a single photodiode could be used in the system. However, such a device would not be as stable as the preferred embodiment. Additionally, such an alternate embodiment would need to account for the temperature response of the photodiode, which is automatically canceled out by the matching photodiode in the preferred embodiment described above.

While the measurement circuitry 54 is shown as being separate from the digital computer 66, it is also contemplated that the measurement circuitry can be incorporated into the digital computer as hardware or software. Similarly, the functions of the digital computer, storage, calculation of viscosity, temperature correction, and/or data display can be incorporated into the measurement circuitry.

Figure 4:
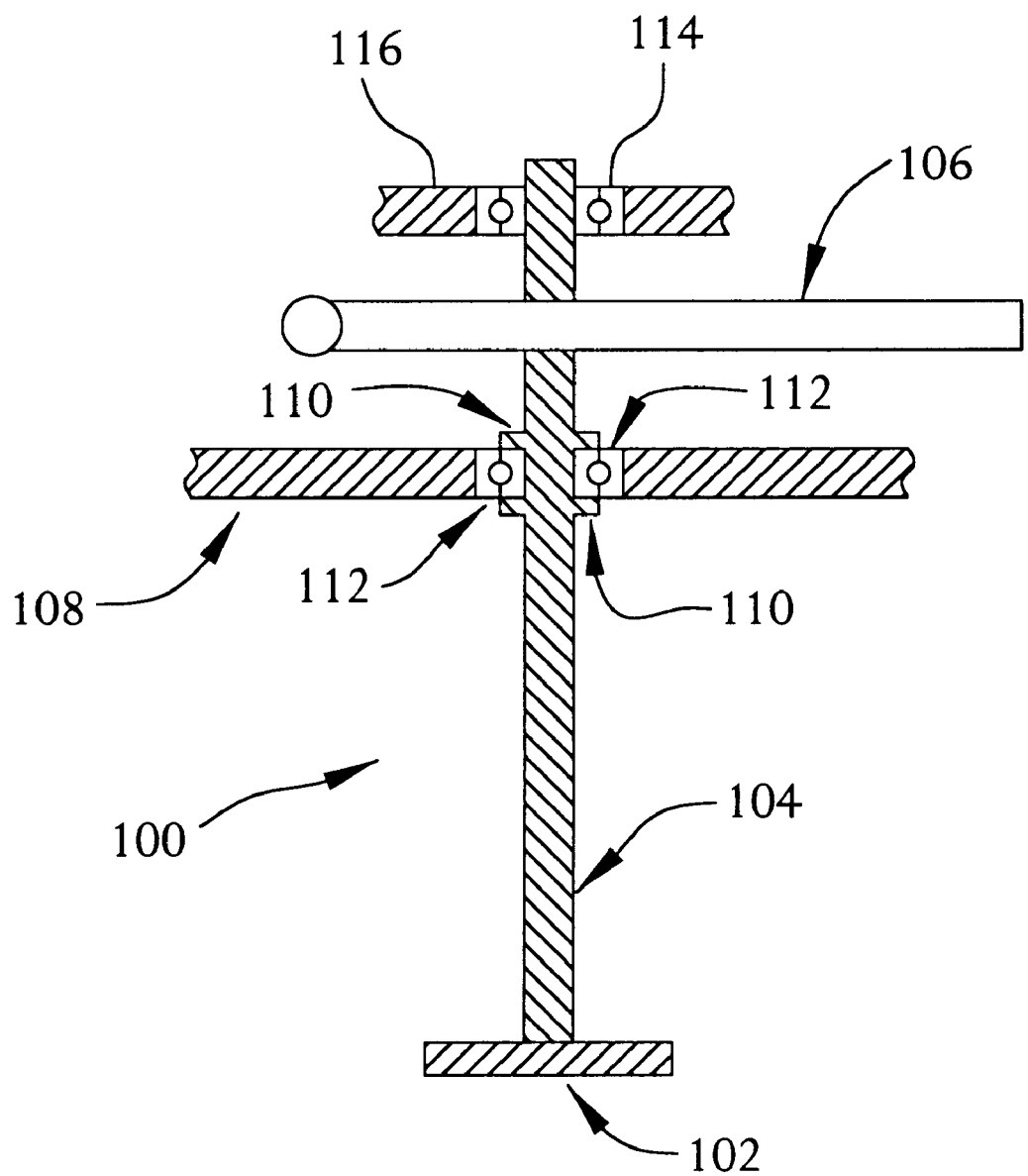
FIG. 4 is a partial view of the measurement arm as attached to a shaft supported by two bearings in viscometer housing.

Referring now to FIG. 4, another embodiment of the invention is shown generally designated as 100. In this embodiment, a measurement disk 102 is mounted to a haft 104 which, in turn, is mounted directly to the measurement arm 106. The shaft 104 is supported by the housing 108. More specifically, flanges 110 are formed on the shaft 104 and engage with opposite sides of the housing 108, retaining the shaft 104. In order to permit the shaft 104 to rotate freely with respect to the housing 108, a high quality bearing 112 is disposed between the housing 108 and the shaft 104. In order to ensure a robust design, a second bearing 114 can be mounted between the shaft 104 and an upper support 116.

As discussed above, the present invention operates similar to an analytical balance. An analytical balance routinely have a capacity of 200 grams and a resolution of 0.0001 grams, resulting in a dynamic range of one part in 2 million. It is a reasonable prediction that resolution of the present invention will be approximately one part in 10,000 to 100,000 if the temperature of the sample is controlled accurately. In comparison, prior art spring-type balances have a dynamic range of only one part in 100. Hence, the present invention provides 100 to 1000 times better accuracy than prior art spring-type viscometers.

Although the invention has been described and illustrated with respect to the exemplary embodiments thereof, it should be understood by those skilled in the art that the foregoing and various other changes, omissions and additions may be made therein and thereto, without parting from the spirit and scope of the present invention.

What is claimed is:

1. a rotational viscometer for measuring the viscosity of a rotating fluid comprising:
    a measurement disk adapted to be located within a fluid being measured;
    at least one shaft extending upward from the disk;
    a support block attached to the at least one shaft;
    two displacement shafts extending upward from the support block;
    a measurement arm mounted within a housing, the measurement arm having a center of rotation, the displacement shafts attaching to the measurement arm on opposite sides of the measurement arm's center of rotation, the measurement arm adapted to be rotated about its center of rotation by the displacement shafts when the measurement disk is rotated by the rotating fluid;
    a light source for emitting a beam of light;
    at least two light receivers operably positioned to receive the beam of light, each light receiver providing an output signal which is a function of the amount of light received;
    wherein a portion of the measurement arm is movably disposed between the light source and the at least two light receivers and within the beam of light;
    a signal processor for receiving the output signals from the light receivers, the signal processor for determining a restorative signal as a function of the output signals;
    a balance coil adapted to receive the displacement signal, the balance coil surrounded at least partially by a permanent magnet, the balance coil adapted to generate an electromagnetic field when the restorative signal is non-zero;
    an adjustment shaft engaged with the balance coil and mounted at one end to the measurement arm, the adjustment shaft adapted to translate with the balance coil when the balance coil generates an electromagnetic field, the translation of the adjustment shaft adapted to rotate the measurement arm about its center of rotation in a direction opposite the direction of rotation of the measurement arm caused by rotation of the measurement disk; and
    an output device adapted to receive the restorative signal and provide a viscosity value which is a function of the displacement signal.

2. A rotational viscometer according to claim 1 wherein the output device is a digital computer which determines the viscosity of the sample as a function of the restorative signal.

3. A rotational viscometer according to claim 2 further comprising a temperature probe for determining the temperature of fluid, the temperature probe adapted to be disposed within the fluid and to output a temperature signal; wherein the digital computer is adapted to receive the temperature signal, the digital computer including at least one temperature-to-viscosity profile, the digital computer determining the viscosity of the fluid as a function of the temperature signal, the restorative signal and the at least one temperature-to-viscosity profile.

4. A rotational viscometer according to claim 1 wherein the mounting of the measurement arm to the housing includes a bearing block which is attached to the housing, the bearing block including first and second bearings, and a pivot shaft rotatably positioned between the first and second bearings, the measurement arm being attached to the pivot shaft so as to rotate with it.

5. A rotational viscometer according to claim 4 wherein the first and second bearings are jeweled bearings, and wherein the pivot shaft has first and second conical surfaces which rotatably interact with the first and second jeweled bearings respectively.

6. A rotational viscometer according to claim 1 wherein the signal processor includes a current-to-voltage converter connected to each light receiver for converting the output signal to a voltage, a summing amplifier for receiving the voltages from the converters, and a power amplifier for amplifying the summed voltage and producing the restorative signal.

7. A rotational viscometer for measuring the viscosity of a moving fluid comprising:
    a measurement disk adapted to be located within a moving fluid being measured, the movement of the fluid adapted to impose a rotational force on the measurement disk;
    a light source for emitting a beam of light;
    at least two light receivers positioned to receive the beam of light, each light receiver providing an output signal which is a function of the amount of light received;
    a measurement arm rotatably mounted within a housing, the measurement arm having a center of rotation, the measurement arm being attached to the measurement disk such that rotation of the measurement disk produces concomitant rotation of the measurement arm, a portion of the measurement arm being located between the light source and the at least two light receivers and within the beam of light when the measurement arm is in a non-rotated position;
    a signal processor for receiving the output signals from the light receivers, the signal processor for determining a restorative signal as a function of a change in the output signals; and
    an electromagnetic device adapted to receive the restorative signal, the electromagnetic device interconnected with the measurement arm and adapted to counter-rotate the measurement arm in response to the restorative signal, the amount of rotation being a function of the amplitude of the restorative signal.

8. A rotational viscometer according to claim 7 further comprising an output device adapted to receive the restorative signal and provide a viscosity value which is a function of the restorative signal.

9. A rotational viscometer according to claim 7 wherein the output device is a digital computer which determines the viscos of the sample as a function of the restorative signal.

10. A rotational viscometer according to claim 9 further comprising a temperature probe for determining the temperature of the fluid, the temperature probe adapted to be disposed within the fluid and to output a temperature signal;

wherein the digital computer is adapted to receive the temperature signal, the digital computer including at least one temperature-to-viscosity profile, the digital computer determining the viscosity of the fluid as a function of the temperature signal, the restorative signal and the at least one temperature-to-viscosity profile.

11. A rotational viscometer according to claim 7 wherein the mounting of the measurement arm to the housing includes a bearing block which is attached to the housing, the bearing block including first and second bearings, and a pivot shaft rotatably positioned between the first and second bearings, the measurement arm being attached to the pivot shaft so as to rotate with it.

12. A rotational viscometer according to claim 11 wherein the first and second bearings are jeweled bearings, and wherein the pivot shaft has first and second conical surfaces which rotatably interact with the first and second jeweled bearings respectively.

13. A rotational viscometer according to claim 7 wherein the signal processor includes a current-to-voltage converter connected to each light receiver for converting the output signal to a voltage, a summing amplifier for receiving the voltages from the converters, and a power amplifier for amplifying the summed voltage and producing the displacement signal.

14. A rotational viscometer according to claim 7 wherein the attachment of the measurement-arm to the measurement disk includes:

a shaft attached to and extending upward from the measurement disk;

a support block mounted to an upper end of the shaft and having a center of rotation coincident with the measurement disk;

two displacement shafts mounted to and extending upward from the top of the support block, the displacement shafts being located equidistant from and on diametrically opposed sides of the center of rotation of the support block the displacement shafts being attached to the measurement arm on opposite sides of the measurement arm's center of rotation.

15. A rotational viscometer according to claim 7 further comprising:

a motor;

a turntable mounted to the motor, the motor adapted to rotate the turntable at a predetermined speed; and a container removably positioned on the turntable and adapted to contain the fluid being measured.

16. A rotational viscometer according to claim 7 wherein the electromagnetic device includes an adjustment shaft that is linearly translated in response to he restorative signal.

17. A rotational viscometer according to claim 7 wherein the ectromagnetic device includes a magnet and a coil, and wherein the restorative signal energizes the coil to induce counter-rotation of the measurement arm.

18. A rotational viscometer for measuring the viscosity of a rotating fluid comprising:

a measurement disk adapted to be located within a rotating fluid being measured, the rotating fluid adapted to subject the measurement disk to a rotational force;

a light source for emitting a beam of light;

at least one light receiver positioned to receive the beam of light, the light receiver providing an output signal which is a function of the amount of light received;

a measurement component rotatably mounted within a housing, the measurement component having a center of rotation and being attached to the measurement disk such that rotation of the measurement disk produces concomitant rotation of the measurement component, a portion of the measurement component being located between the light source and the light receiver such that rotation of the measurement component alters the amount of light that passes the measurement component and is received by the light receiver;

a signal processor for receiving the output signal from the light receiver, the signal processor determining a restorative signal as a function of a change in the output signal;

a restoring device adapted to receive the restorative signal and counter-rotate the measurement component in response to the restorative signal, the amount of counter-rotation being a function of the amplitude of the restorative signal; and a display for displaying the viscosity of the fluid being measured as a function of the restorative signal.

19. A method for determining the viscosity of a fluid comprising the steps of:

illuminating two photodiodes with a light source;

rotating a sample of fluid in container, the rotation of the fluid causing a measurement disk contained within the fluid to rotate in the same direction as the fluid;

displacing a measurement component as a function of the rotation of the measurement disk, the displacement of the measurement component causing a portion of the measurement component to move between the light source and the photodiodes thereby altering the amount of light received by the photodiodes;

measuring the amount of light received by the photodiodes and providing output signals indicative thereof;

determining a restorative signal as a function of a change in the output signals;

counter-rotating the measurement component when the restorative signal is non-zero, the amount of counter-rotation being a function of the amplitude of the restorative signal;

converting the restorative signal to a viscosity; and displaying the viscosity.

\* \* \* \* \*